United States Patent
Egido De Los Rios et al.

(10) Patent No.: US 10,532,082 B2
(45) Date of Patent: Jan. 14, 2020

(54) SOCS1-DERIVED PEPTIDE FOR USE IN CHRONIC COMPLICATIONS OF DIABETES

(71) Applicants: Fundació Hospital Universitari Vall d'Hebron-Institut de Recerca, Barcelona (ES); Fundación Instituto de Investigación Sanitaria Fundación Jiménez Díaz, Madrid (ES); Universidad Autónoma De Madrid, Madrid (ES)

(72) Inventors: Jesús Egido De Los Rios, Madrid (ES); Carmen Gómez Guerrero, Madrid (ES); Rafael Simó Canonge, Barcelona (ES); Cristina Hernández Pascual, Barcelona (ES)

(73) Assignees: Fundació Hospital Universitari Vall d'Hebron-Institut de Recerca, Barcelona (ES); Fundación Instituto de Investigación Sanitaria Fundación Jiménez Díaz, Madrid (ES); Universidad Autónoma De Madrid, Madrid (ES)

( * ) Notice: Subject to any disclaimer, the term of this patent is extended or adjusted under 35 U.S.C. 154(b) by 0 days.

(21) Appl. No.: 15/314,395

(22) PCT Filed: May 27, 2015

(86) PCT No.: PCT/ES2015/070415
§ 371 (c)(1),
(2) Date: Nov. 28, 2016

(87) PCT Pub. No.: WO2015/181427
PCT Pub. Date: Dec. 3, 2015

(65) Prior Publication Data
US 2017/0209536 A1    Jul. 27, 2017

(30) Foreign Application Priority Data
May 28, 2014   (ES) .................................. 201430796

(51) Int. Cl.
*A61K 38/17* (2006.01)
*A61K 9/00* (2006.01)
*A61K 38/10* (2006.01)
*A61K 47/54* (2017.01)

(52) U.S. Cl.
CPC ........ *A61K 38/1709* (2013.01); *A61K 9/0048* (2013.01); *A61K 38/10* (2013.01); *A61K 47/542* (2017.08)

(58) Field of Classification Search
CPC .. A61K 38/00; A61K 47/542; A61K 38/1709; A61K 38/10
See application file for complete search history.

(56) References Cited

U.S. PATENT DOCUMENTS

| 2009/0030179 A1 | 1/2009 | Yoshida et al. |
| 2009/0209458 A1 | 8/2009 | Hawiger et al. |
| 2009/0253618 A1 | 10/2009 | Kanno et al. |

FOREIGN PATENT DOCUMENTS

| WO | WO-2010151495 | 12/2010 |
| WO | WO-2015181427 | 12/2015 |

OTHER PUBLICATIONS

Mattern, Ralph-Heiko, et al., "Effect of RGD Peptides in In Vivo Model for Diabetic Retinopathy", Peptide Revolution: Genomics, Proteomics & Therapeutics. The proceedings of the 18th American Peptide Symposium, Boston, MA, (709-710), Jul. 19, 2003.
"International Application No. PCT/ES2015/070415, International Search Report and Written Opinion dated Sep. 11, 2015", (Sep. 11, 2015), 12 pgs.
Ahmed, Chulbul M., et al., "SOCS-1 Mimetics Protect Mice against Lethal Poxvirus Infection: Identification of a Novel Endogenous Antiviral System", Journal of Virology, vol. 83, No. 3, Feb. 2009, p. 1402-1415, (Feb. 2009), 1402-1415.
Anderson, Peter JB, et al., "Glial and endothelial blood-retinal barrier responses to amyloid-b in the neural retina of the rat", Clinical Ophthalmology 2008:2(4) 801-816, (2008), 801-816.
Bogdanov, Patricia, et al., "The db/db Mouse: A Useful Model for the Study of Diabetic Retinal Neurodegeneration", PLoS One, vol. 9, No. 5, May 2014, e97302, (May 2014), 18 pgs.
Cunha-Vaz, José, "The Blood—Retinal Barrier in Retinal Disease", European Ophthalmic Review—2009, vol. No. 3, pp. 105-108, (2009), 105-108.
Flodstrom-Tullberg, Malin, et al., "Target Cell Expression of Suppressor of Cytokine Signaling-1 Prevents Diabetes in the NOD Mouse", Diabetes, vol. 52, Nov. 2003, (Nov. 2003), 2696-2700.
Girolami, Elizabeth I., et al., "Differential expression and potential role of SOCS1 and SOCS3 in Wallerian degeneration in injured peripheral nerve", Exp Neurol. May 2010; 223(1): 173-182, (May 2010), 173-182.

(Continued)

*Primary Examiner* — James H Alstrum-Acevedo
*Assistant Examiner* — Kaipeen E Yang
(74) *Attorney, Agent, or Firm* — Schwegman Lundberg & Woessner, P.A.

(57) ABSTRACT

The present invention relates to a SOCS1-derived peptide for use in chronic complications of diabetes, particularly ocular, renal, nerve and vascular complications, as well as compositions containing same and isolated polynucleotides encoding same. The present invention also relates to the SOCS1-derived peptide for topical use in the treatment and/or prevention of neurodegenerative diseases of the retina, particularly in the early stages of diabetic retinopathy and other diseases of the retina in which neurodegeneration plays an essential role.

15 Claims, 14 Drawing Sheets
Specification includes a Sequence Listing.

(56) References Cited

OTHER PUBLICATIONS

Jager, Lindsey D., et al., "The Kinase Inhibitory Region of SOCS-1 is Sufficient to Inhibit Thelper 17 and other Immune Functions in Experimental Allergic Encephalomyelitis", J Neuroimmunol. Mar. 2011; 232(1-2): 108-118, (108-118), Mar. 2011.

Liang, Xiao, et al., "Multiple roles of SOCS proteins: Differential expression of SOCS1 and SOCS3 in atherosclerosis", International Journal of Molecular Medicine 31: 1066-1074, 2013, (Feb. 1, 2013), 1066-1074.

Marmor, Michael F., et al., "Standard for clinical electroretinography (2004 update)", Documenta Ophthalmologica 108: 107-114, 2004, (2004), 107-114.

Mujtaba, Mustafa G., et al., "Treatment of Mice with the Suppressor of Cytokine Signaling-1 Mimetic Peptide, Tyrosine Kinase Inhibitor Peptide, Prevents Development of the Acute Form of Experimental Allergic Encephalomyelitis and Induces Stable Remission in the Chronic Relapsing/Remitt", J Immunol 2005; 175:5077-5086, (2005), 5077-5086.

Ortiz-Munoz, Guadalupe, et al., "Suppressors of Cytokine Signaling Modulate JAK/STAT-Mediated Cell Responses During Atherosclerosis", Arterioscler Thromb Vasc Biol. 2009;29:525-531, (2009), 525-531.

Ortiz-Muñoz, Guadalupe, et al., "Suppressors of Cytokine Signaling Abrogate Diabetic Nephropathy", J Am Soc Nephrol. May 2010; 21(5): 763-772, (May 2010), 763-772.

Schmidt, K.-G., et al., "Neurodegenerative Diseases of the Retina and Potential for Protection and Recovery", Current Neuropharmacology, 2008, vol. 6, No. 2, (164-178), 2008.

Wesoly, Joanna, et al., "Suppressor of cytokine signaling and accelerated atherosclerosis in kidney disease", Acta Biochim Pol 2010; 57(3):251-260, (2010), 251-260.

Yu, Cheng-Rong, et al., "Suppressor of Cytokine Signaling-1 (SOCS1) Inhibits Lymphocyte Recruitment into the Retina and Protects SOCS1 Transgenic Rats and Mice from Ocular Inflammation", Investigative Ophthalmology & Visual Science, Aug. 2011, vol. 52, No. 9, (Aug. 31, 2011), 9 pgs.

Figure 2

| score | GFAP immunofluorescence degree (%) | | |
|---|---|---|---|
| | D-SHAM (eye drops) | D-SOCS M151 (eye drops) | control (db/+) |
| 1 | 0.00 | 62.50 | 60.00 |
| 2 | 0.00 | 12.50 | 45.50 |
| 3 | 23.00 | 25.00 | 5.00 |
| 4 | 10.00 | 0.00 | 0.00 |
| 5 | 67.00 | 0.00 | 0.00 |

SOCS1-DERIVED PEPTIDE FOR USE IN CHRONIC COMPLICATIONS OF DIABETES

PRIORITY CLAIM TO RELATED APPLICATIONS

This application is a U.S. national stage application filed under 35 U.S.C. § 371 from International Application Serial No. PCT/ES2015/070415, which was filed 27 May 2015, and published as WO2015/181427 on 3 Dec. 2015, and which claims priority to Spanish Application No. P201430796, filed 28 May 2014, which applications and publication are incorporated by reference as if reproduced herein and made a part hereof in their entirety, and the benefit of priority of each of which is claimed herein.

OBJECT OF THE INVENTION

The present invention relates to a SOCS1-derived peptide useful for the prevention and treatment of chronic complications of diabetes, particularly ocular, renal, nerve and vascular complications. Diabetic retinopathy and macular edema are included within the area of eye complications of diabetes. Given the neuroprotective nature of the SOCS1-derived peptide, the present invention is also considered potentially effective for other diseases of the retina, besides diabetic retinopathy, in which neurodegeneration plays a fundamental role such as acquired or inherited neurodegenerative diseases of the retina.

BACKGROUND OF THE INVENTION

Diabetes mellitus is a highly prevalent systemic disease that often causes lesions in several organs, particularly the retina, kidney, nerves and vascular system. Diabetes complications are usually divided into: a) acute complications, such as hypoglycemia, ketoacidosis and hyperosmolar coma; b) chronic or late complications, in turn divided into microangiopathic complications (nephropathy, retinopathy, and neuropathy), macroangiopathic complications (cardiovascular disease) and diabetic foot (macro- and microangiopathy).

The enormous social-health impact of diabetes is due to these chronic complications, mainly ocular (retinopathy), renal (nephropathy) and vascular (atherosclerosis) complications. Current approaches for treating diabetes, such as strict glucose and hypertension control, successfully stop disease progression but do not prevent the onset of chronic complications in many cases, particularly retinopathy, cardiovascular events or the progression of patients to renal failure and even their participation in dialysis and transplant programs.

Diabetic foot is one of the most common complications of diabetes which causes significant morbidity and a high risk of amputation and the treatment of which requires a multidisciplinary approach.

Diabetic retinopathy is the most common complication of diabetes and one of the main causes of blindness worldwide. Hyperglycemia per se and the metabolic pathways directly related to it intervene in the etiopathogenesis of diabetic retinopathy, causing damage in the capillary bed located in the inner retina (microangiopathic lesion). Diabetic retinopathy has been conventionally considered as a microangiopathic disease of the retina. However, current evidence indicates that neurodegeneration is an early phenomenon in the pathogenesis of diabetic retinopathy participating in the development of microvascular alterations. There are currently no specific treatments for the initial phases of diabetic retinopathy. Furthermore, the specific treatments indicated in advanced phases of the disease (laser photocoagulation, intravitreal injections of agents such as the anti-VEGF—"vascular endothelial growth factor" antibodies—or corticoids or vitrectomy) have a limited effectiveness and a high rate of side effects. Non-invasive therapeutic approaches would be necessary to prevent or treat diabetic retinopathy in the initial phases (neurodegeneration). In this sense, topical ocular administration (eye drops) would be the most suitable route due to its non-invasive nature as it would prevent systemic side effects.

In addition to diabetic retinopathy, there are other diseases presenting with neurodegeneration of the retina such as age-related macular degeneration (AMD), glaucoma and retinitis pigmentosa. Neurodegenerative diseases of the retina refer to the conditions of the retina characterized by progressive neuronal loss.

An in-depth analysis of these diseases, their critical sites, as well as the possible ways of protection and paths leading to recovery can be extracted from Schmidt et al., "Neurodegenerative Diseases of the Retina and Potential for the Protection and Recovery", *Current Neuropharmacology*—2008, Vol. No. 6, pp.: 164-178.

In the case of diabetic retinopathy, neurodegeneration (loss of effective neurons) occurs in the early stages of the disease and causes functional abnormalities, such as the loss of chromatic discrimination and contrast sensitivity. These alterations can be detected by means of electrophysiological studies in diabetic patients even with less than two years of having diabetes, i.e., before the microvascular lesions can be detected under ophthalmologic examination. Furthermore, a delayed multifocal electroretinogram implicit time (mfERG-IT) predicts the development of early microvascular abnormalities. In addition, neuroretinal degeneration initiates and/or activates several metabolic and signaling pathways that will participate both in the microangiopathic process and in the disruption of the blood-retinal barrier (BRB).

The BRB is a structure of the eye that is very important in many diseases of the retina and, particularly, it is a crucial element in the pathogenesis of diabetic retinopathy. The BRB is made up of an inner BRB and an outer BRB. The inner BRB is formed by tight endothelial cell junctions. The outer BRB is made up of retinal pigment epithelium (RPE), the cells of which are also connected by tight junctions. Diabetic macular edema is due to the disruption of the BRB. Another common disease of the retina due to deterioration of the BRB which results in retinal edema is AMD. Furthermore, alteration of the BRB also occurs in many ocular situations, such as uveitis, trauma, intra-ocular surgery, vascular retinopathies, inherited dystrophies, etc. (Cunha-Vaz et al., "The Blood-Retinal Barrier in Retinal Disease", *European Ophthalmic Review*—2009, Vol. No. 3, pp.:105-108).

Great effort is being made in recent years to know the molecular mechanisms involved in the development of diabetes complications, as well as to study their therapeutic potential.

The JAK/STAT (Janus Kinase/Signal Transducers and Activators of Transcription) signaling pathway is an important intracellular mechanism through which hyperglycemia and other factors contribute to the development of diabetes and its complications. JAK/STAT controls many cellular processes, such as proliferation, migration and differentiation, as well as the expression of inflammatory mediators. An increase in the expression and activation of members of the JAK/STAT pathway in atheromatous plaques, in renal biopsies of diabetic patients and in animal models of retinopathy and diabetic nephropathy has been described.

The SOCS (Suppressors Of Cytokine Signaling) protein family is the main endogenous mechanism for the negative regulation of the JAK/STAT pathway and alterations in the expression levels have been linked to different immune and inflammatory diseases. Experimental studies in genetically modified animals for SOCS family members have demonstrated a protective effect in pancreatic β-cells, with reduction in the incidence of diabetes (Flodström-Tullberg et al., *Diabetes* 2003; 52:2696-700) and in the associated renal damage (Ortiz-Muñoz et al., *J Am SocNephrol* 2010; 21:763-72), as well as an anti-atherosclerotic effect (Ortiz-Muñoz et al., *ArteriosclerThromb Vasc Biol* 2009; 29:525-531; Wesoly et al., *Acta Biochim Pol* 2010; 57(3):251-260; Liang et al., *Int J Mol Med.* 2013 May; 31(5):1066-74). This suggests a therapeutic potential of these endogenous proteins in diabetes complications.

The use of SOCS protein mimetic peptides has been described previously in experimental allergic encephalomyelitis, a model of multiple sclerosis (Mujtaba et al., *J Immunol* 2005; 175:5077-5086; Jager et al., *J Neuroimmunol* 2011; 232:108-118) and also in models of peripheral nerve damage (Girolami et al., *ExpNeurol* 2010; 223:173-182) and poxvirus viral infection (Ahmed et al., *J Virol* 2009; 83:1402-1415). SOCS polypeptides have also been described as inhibitors of cytokine-induced signaling, particularly in inflammation and viral or bacterial infections (US2009/0209458). Patent publication WO2010/151495 describes SOCS-1 or SOCS-3 antagonist peptides useful as antivirals. Patent document U.S. Pat. No. 8,420,096 describes a soluble peptide containing the SOCS1/SOCS3 sequence and a membrane translocation sequence and the potential use thereof for the treatment of immune diseases. Patent document US2009253618 also describes peptides of this type for use thereof in neuronal differentiation. Patent document US2009030179 uses several synthetic peptides of the SOCS-box region of these peptides as antimicrobial agents.

Despite the research existing in this field and the fact that the relationship between the JAK/STAT signaling pathway, SOCS proteins and diabetes has been postulated, the effective administration of a peptide per se for the prevention or treatment of ocular, renal or vascular complications of diabetes has not been described up until now. SOCS mimetic peptides have not been linked in any case to ocular disorders.

BRIEF DESCRIPTION OF THE INVENTION

It has been found that a polypeptide corresponding to a region of the SOCS1 protein is effective for the treatment of chronic complications of diabetes in vivo in animal models of diabetes.

Additionally, it has been found that said polypeptide is effective in the treatment of neurodegenerative diseases of the retina.

Therefore, in a first aspect the present invention relates to an isolated polypeptide containing
a) the sequence of SEQ ID NO 2 (DTHFRTFRSHADYRRI); or
b) a variant of the sequence of a) which is at least 85% identical to SEQ ID NO 2, based on the identity of all the amino acids of said sequence;
for the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

In a second aspect, the present invention relates to a composition comprising a therapeutically effective amount of a polypeptide of the first aspect and at least one pharmaceutically acceptable vehicle or excipient, for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

In a third aspect, the present invention relates to an isolated polynucleotide encoding
a) the amino acid sequence SEQ ID NO 2; or
b) a variant of the sequence of a) or b) which is at least 85% homologous to the sequence SEQ ID NO 2;
for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

An additional aspect of the invention is the use of an isolated polypeptide containing
a) the sequence of SEQ ID NO 2 (DTHFRTFRSHADYRRI); or
b) a variant of the sequence of a) which is at least 85% identical to SEQ ID NO 2, based on the identity of all the amino acids of said sequence;
for the preparation of a medicament for the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

The invention also relates to an isolated polynucleotide encoding
a) the amino acid sequence SEQ ID NO 2; or
b) a variant of the sequence of a) which is at least 85% homologous to the sequence SEQ ID NO 2;
for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

It also relates to the use of an isolated polynucleotide encoding
a) the amino acid sequence SEQ ID NO 2; or
b) a variant of the sequence of a) which is at least 85% homologous to the sequence SEQ ID NO 2;
for the preparation of a medicament for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

In a last aspect, the invention relates to a treatment method, which comprises administering a therapeutically effective amount of a polypeptide of the first aspect to a patient with chronic complications of diabetes and/or suffering neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where said neurodegenerative diseases of the retina are selected from the group consisting of diabetic retinopathy, glaucoma and retinitis pigmentosa.

These compounds act as topical neuroprotective agents of the retina. It must be pointed out that the topical administration of peptides for use according to the invention does not only reach the retina, but rather also achieves effective concentrations to prevent the progression of diabetic retinopathy.

BRIEF DESCRIPTION OF THE DRAWINGS

FIG. 2. Effect of the topical administration (eye drops) of the SOCS1-derived peptide on glial activation: Glial activation quantification based on the measurement of GFAP (Glial fibrillar acidic protein) staining in the retina in representative samples from a diabetic mouse treated with the vehicle [D-Sham], a diabetic mouse treated with eye drops containing the SOCS1-derived peptide [D-SOCSM1S1] and a non-diabetic mouse [control (db/+)].

DETAILED DESCRIPTION OF THE INVENTION

Figure 1:
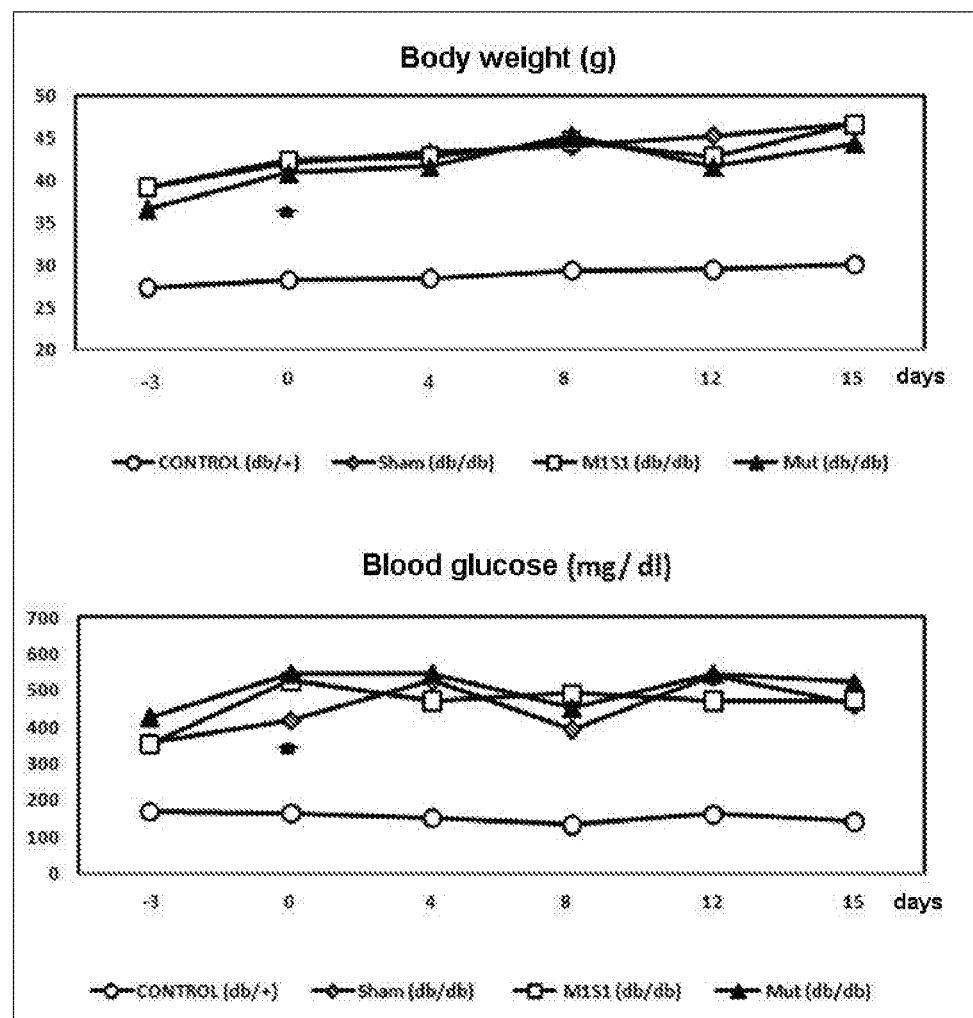
FIG. 1. Progression of glycemia and weight in the model of diabetic retinopathy. Blood glucose level (A) and body weight (B) throughout the study. Treatment with inhibitory peptide did not affect these parameters.

As indicated above, the first aspect of the invention relates to an isolated polypeptide containing
a) the sequence of SEQ ID NO 2 (DTHFRTFR-SHADYRRI); or
b) a variant of the sequence of a) which is at least 85% identical to SEQ ID NO 2, based on the identity of all the amino acids of said sequence;
for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, age-related macular degeneration, glaucoma and retinitis pigmentosa.

One or more of the amino acids of any of the sequences mentioned in the present invention, particularly SEQ ID NO 1, SEQ ID NO 2 and SEQ ID NO 3, can be modified, for example, they can be phosphorylated. According to a particular embodiment, only one amino acid of the sequence is modified, preferably phosphorylated. According to a preferred embodiment, the phosphorylated amino acid is the tyrosine (Y).

In the scope of the present invention, the term "% of identity" or "at least % identical", in relation to amino acid sequences, means the percentage of identity determined by means of the following method: alignment of two amino acid sequences performed by means of the service provided in https://www.ebi.ac.uk/Tools/msa/clustalw2/, applying the default adjustments of this service. Therefore, for example, SEQ ID NO 1 would be a variant of the sequence of SEQ ID NO as it is defined herein.

In the scope of the present invention, the term "chronic complications of diabetes" shall be understood as encompassing, but is not necessarily limited to, ocular, renal, nerve and vascular complications or disorders, the term "vascular" being herein understood as encompassing both cardiovascular and cerebrovascular complications. Specifically, it would include complications selected from diabetic retinopathy, macular edema, diabetic nephropathy, diabetic angiopathies, including microangiopathies and macroangiopathies, such as diabetic atherosclerosis, diabetic foot and peripheral artery disease. Therefore, the peptide of the invention is for use in the prevention or treatment of chronic complications of diabetes selected from the group consisting of ocular, renal, nerve and cardiovascular complications or disorder in diabetic patients.

Therefore, in a particular embodiment the chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease. According to a preferred embodiment, the chronic complication of diabetes is an ocular disorder, particularly diabetic retinopathy.

The peptide of the invention is also useful in the treatment of neurodegenerative diseases of the retina. In the scope of the present invention, the term "neurodegenerative diseases of the retina" shall be understood as encompassing those ocular pathologies which are characterized by the presence of glial inflammation (glial activation or reactive gliosis) due to progressive neuronal death by apoptosis of the retinal neurons, specifically the photoreceptors, which can result in blindness consequently. Examples of said diseases include, but are not limited to, diabetic retinopathy, glaucoma and retinitis pigmentosa. According to a particular embodiment of the present invention, said diseases are selected from a group consisting of diabetic retinopathy, glaucoma and retinitis pigmentosa. According to a preferred embodiment, the neurodegenerative disease of the retina is diabetic retinopathy.

In the sense of the invention, the term "neuroprotection" shall be understood as encompassing, but is not necessarily limited to, any type of prophylactic treatment or method that can be used so that neurons forming the neuroretina are preserved in a physiological state corresponding to that of a healthy animal subject (including humans). The "neuroretina" is the neurosensory part of the retina and is responsible for visual cycle.

Particularly, the peptide "for topical use in the treatment and/or prevention" according to the invention shall be understood as encompassing, but is not necessarily limited to, ocular topical use in the treatment and/or prevention, specifically, of a neurodegenerative disease of the retina selected from the group consisting of diabetic retinopathy, glaucoma and retinitis pigmentosa.

According to a particular embodiment, the variant of the sequence SEQ ID NO 2 is at least 90% identical, even more preferably about 94% identical, a figure which would correspond, for example, to the substitution of one amino acid with another in the sequence SEQ ID NO 2, or the addition of one amino acid to the sequence SEQ ID NO 2. According to a particular embodiment, the variant would be SEQ ID NO 1 (DTHFRTFRSHSDYRRI). Other mammal species, such as *Rattus Norvergicus, Gorilla gorilla gorilla, Oryctolagus cuniculus, Pan troglodytes, Pongo abelii, Cavia porcellus* or *Sus scrofa*, have SEQ ID NO 1 or SEQ ID NO 2, since this sequence is highly conserved among mammal species.

According to a preferred embodiment, such sequence SEQ ID NO 2 or the variants thereof which are identical in a percentage as defined above, is bound to a cell permeability region. Said cell permeability region can be selected from different described permeability sequences, generally small cationic or hydrophobic peptides, such as TAT (SEQ ID NO 4: YGRKKRRQRRR), Antp (SEQ ID NO 5: RQIKIWFQN-RRMKW), PTD-5 (SEQ ID NO 6: RRQRRTSKLMKR), SEQ ID NO 7: 8K (K=Lys) and SEQ ID NO 8: 6R (R=Arg). More preferably, the cell permeability region is a lysine-palmitate region. Even more preferably, the cell permeability region is bound at the amino terminal end of the SEQ ID NO 2 or the identical variants thereof.

Any polypeptide comprising the mentioned sequence or the identical variants thereof as defined above is included in the scope of the invention. However, according to a preferred embodiment the polypeptide consists essentially of
a) the sequence of SEQ ID NO 2; or
b) a variant of the sequence of a) which is at least 85% identical to SEQ ID NO 2, based on the identity of all the amino acids of said sequence.

Particularly, the variant will consist of the sequence SEQ ID NO 1.

In the scope of the present invention, the term "consists essentially of" refers to the inclusion of a maximum of 8 additional amino acids (in other words, a maximum of 50% more) to the defined sequences or the homologous variants thereof, according to preferred embodiments, a maximum of 7, 6, 5, 4, 3, 2 or 1 additional amino acids, which can be bound independently to amine end of the sequence, to the acid end or in any site of the sequence, becoming part of the sequence.

In any of the preceding cases, the sequence may or may not be bound to a cell permeability region as defined above.

According to a particular embodiment, the polypeptide consists of the sequence SEQ ID NO 2; may or may not be bound to a cell permeability region as defined above.

In the case that the polypeptide is for use in ocular complications in diabetic patients, or for use in degenerative diseases of the retina such as diabetic retinopathy, the polypeptide containing the sequence of SEQ ID NO 2 or the identical variants thereof as defined above according to a particular embodiment consists essentially of or is:
a) the human SOCS1 protein (UniProt: 015524);
b) the murine SOCS1 protein (UniProt: 035716); or
c) a variant of the sequences of a) or b) which is at least 85% identical to the amino acid sequence of the murine SOCS1 protein or to the amino acid sequence of the human SOCS1 protein.

Like any of the preceding particular embodiments, at least one of the amino acids of the human or murine SOCS1 protein, or an identical variant thereof, can be modified, preferably phosphorylated. According to a preferred embodiment, the phosphorylated amino acid or one of the phosphorylated amino acids will be a tyrosine (Y). Likewise, the SOCS1 protein according to the preceding definitions can be bound to a cell permeability region, preferably to a palmitate-lysine group. According to a preferred embodiment, the cell permeability region is bound at the N-terminal end of the polypeptide, the cell permeability region being more preferably a palmitate-lysine group.

The at least 85% identical variant includes the SOCS1 proteins of other mammals, such as *Rattus Norvergicus, Gorilla, Oryctolagus cuniculus, Pan troglodytes, Pongo abelii, Cavia porcellus* or *Sus Scrofa*.

According to particular embodiments, the variant of the human or murine SOCS1 sequences are at least 90% identical, even more preferably about 94% identical, to said sequences.

All the preferred embodiments indicated for this first aspect of the invention are also applicable to the rest of the aspects of the invention, provided in detail below.

An additional aspect of the invention is the use of an isolated polypeptide comprising
a) the sequence of SEQ ID NO 2 (DTHFRTFR-SHADYRRI); or
b) a variant of the sequence of a) which is at least 85% identical to SEQ ID NO 2, based on the identity of all the amino acids of said sequence;
for the preparation of a medicament for the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa.

According to another aspect of the invention, this refers to a composition comprising a therapeutically effective amount of a polypeptide according to any of the preceding definitions, and at least one pharmaceutically acceptable vehicle or excipient, for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa, according to the definitions given above.

In a preferred embodiment of the invention, the composition is suitable for use or is intended for being used in the prevention or treatment of ocular disorders in diabetic patients and/or neurodegenerative diseases of the retina, preferably diabetic retinopathy. It could also be used for other diseases of the retina presenting with neurodegeneration, glaucoma and retinitis pigmentosa.

Therefore, according to a particular embodiment the vehicle or excipient is a pharmaceutically acceptable vehicle or excipient suitable for ophthalmic administration.

The compositions according to the present invention comprise at least one pharmaceutically acceptable vehicle or excipient. The term "pharmaceutically acceptable vehicle or excipient" refers to molecular substances or entities together with which the peptide of the invention is administered. Such vehicles or excipients will be suitable for the chosen route of administration, and will be obvious for a person skilled in the art depending on the route of administration. The vehicles can be sterile liquids, such as water or oils, including those derived from petroleum, those of animal, plant or synthetic origin, excipients, disintegrating agents, wetting agents or diluents. Suitable vehicles and excipients are described, for example in "*Remington's Pharmaceutical Sciences*" of E. W. Martin, which is incorporated herein by reference.

The compositions according to the present invention can be administered through any known route, including orally, gastroenterically, parenterally, rectally, by respiratory route and topically, particularly ophthalmically. Likewise, the compositions may contain other suitable active ingredients or adjuvants which will be obvious for the person skilled in the art. Likewise, the compositions may only contain a single polypeptide according to the invention or two or more polypeptides according to the invention.

In the case of the ophthalmic route, the vehicle or excipient must be suitable for this route of administration. The compositions in this case will be suitably prepared, either as a solution or an aqueous suspension, in a pharmaceutically acceptable ophthalmic base solution or vehicle. In addition to the active ingredient, in this case the polypeptide according to the invention can contain other adjuvants, such as antimicrobial agents, preservatives, chelating agents, tonicity regulating agents, pH regulating agents, including buffer solutions, thickening agents, etc.

If the subject receives compounds that aid in retinal neuroprotection (such as the peptide of the invention) in the early stages of diabetic retinopathy when the functional abnormalities can be detected (i.e., chromatic discrimination, contrast sensitivity and electroretinographic abnormalities), aggressive treatments of the disease can be prevented. Therefore, if the retina is protected from the consequences of chronic hyperglycemia, the main complications can be minimized or the onset thereof can even be prevented, which entails an actual improvement of the quality of life of diabetic patients. In addition, the peptide prevents the disruption of the BRB. Topical ocular administration of the peptides represents a real advantage, preventing more aggressive treatments.

Treatment in the early stages of diabetic retinopathy has the real advantage of preventing additional complications, namely, microaneurysms, microhemorrhages, hard exudates, macular edema and neovascularization.

In the compositions according to the invention, the peptide will be contained in a concentration range of 1-12 mg/mL. In the particular case of ocular administration, the peptide will be contained in a concentration of at least 5 mg/mL, in particular embodiments it will be contained in a concentration of at least 8 mg/mL, at least 9 mg/mL, at least 10 mg/mL, according to a preferred embodiment, in a concentration of 10 mg/mL±5%, i.e., 10 mg/mL±0.5 mg/mL. In the particular case of intraperitoneal administration, the peptide will be contained in a concentration between 1 and 5 mg/mL, according to a particular embodiment it will be contained in a concentration between 1 and 3 mg/mL, according to preferred embodiments, in a concentration of 2 mg/mL±10% or ±5%, i.e., ±0.2 mg/mL or ±0.1 mg/mL.

The composition according to the invention is suitable for the administration of a daily dose of between 10 and 200 µg of peptide per eye. According to a particular embodiment, the peptide will be administered in a daily dose of between 30 and 70 µg per eye, according to a preferred embodiment, in a daily dose of between 40 and 60 µg per eye, preferably between 45 and 55 µg per eye. In the case of intraperitoneal or oral administration, the composition will be suitable for the administration of a daily dose of between 1 and 16 mg of peptide per kg of weight of the patient or subject on which administration is performed, according to particular embodiments, between 2 and 10 mg of peptide per kg of weight of the patient or subject, preferably between 2.5 and 3.5 mg of peptide per kg of weight of the patient or subject.

Another aspect of the invention relates to an isolated polynucleotide encoding
a) the amino acid sequence SEQ ID NO 2; or
b) a variant of the sequence of a) which is at least 85% homologous to the sequence SEQ ID NO 2;
for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa, according to the definitions previously provided.

According to a particular embodiment, the isolated polynucleotide encodes
a) the amino acid sequence SEQ ID NO 2 bound to a lysine group; or
b) a variant of the sequence of a) which is at least 85% identical to the sequence SEQ ID NO 2, bound to a lysine group; for use in the prevention or treatment of chronic complications of diabetes and/or neurodegenerative diseases of the retina, where chronic complications of diabetes are selected from the group consisting of diabetic retinopathy, macular edema, diabetic nephropathy, diabetic angiopathies, diabetic microangiopathies, diabetic macroangiopathies, diabetic atherosclerosis, diabetic foot and peripheral artery disease, and where neurodegenerative diseases of the retina are selected from the group consisting of diabetic retinopathy, glaucoma and retinitis pigmentosa, according to the definitions previously provided.

The polynucleotide defined above is suitable for topical use or is intended for being used topically in the prevention or treatment of the previously mentioned diseases.

Preferably, the polynucleotide defined above is suitable for use thereof or is intended for being used in the prevention or treatment of ocular disorders in diabetic patients and/or neurodegenerative diseases of the retina, more preferably for use thereof in the prevention or treatment of diabetic retinopathy.

A series of non-limiting, illustrative examples of the present invention are included below.

EXAMPLES

Materials and Methods

Peptides:
A peptide of 16 amino acids was synthesized (SEQ ID NO 1: DTHFRTFRSHSDYRRI, AspThrHisPheArgThrPheArg Ser His Ser AspTyrArgArgIle) corresponding to the "kinase inhibitory region" sequence of the murine SOCS1 protein, bound to a cell permeability region (lysine-palmitate) at the N-terminal end of the peptide sequence (residue D, aspartic acid), in which the tyrosine (Y) is phosphorylated. The derived peptide formed by SEQ ID NO 1 and the palmitate-lysine group will be referred to as miS1 or D-SOCSMIS1 throughout the examples. In some cases, the later was conjugated with a fluorescent marker to enable subsequent tracking in tissues and cells. Likewise, non-functional mutated peptide (Mut) substituting F (Phe) with A (Ala) was also synthesized: SEQ ID NO 3, DTHARTARSHSDYRRI, AspThrHisAlaArgThrAla Arg Ser His Ser AspTyrArgArg-Ile; likewise bound to the lysine-palmitate cell permeability region, for use thereof as the control of the experiments. The peptides were dissolved (<1% DMSO in saline solution) and filter-sterilized.

Animals:
Two experimental models, specifically an experimental model of type 2 diabetes (db/db mice) and another experimental model of type 1 diabetes (streptozotocin injection in apoE mice) were used. The mice were kept in standard size cages under controlled temperature (20° C.) and humidity (60%) conditions, with light/darkness cycles of 12 hours and with access to food (standard diet) and water ad libitum. These studies have been conducted according to the Spanish legislation in force in terms of use, protection and care of experimental animals (Royal Decree 53/2013), following the EEC recommendations (86/609/EEC) and ARVO (Association for Research in Vision and Ophthalmology) recommendations and have been previously approved by the Ethics Committee of the two participating institutions (IIS-Fundación Jiménez Diaz/Universidad Autónoma de Madrid and Institut de Recerca Hospital Universitari Vall d'Hebron).

Treatment of Retinal Neurodegeneration Caused by Diabetes by Means of Ocular Topical Treatment With a SOCS1-Derived Peptide 8-week old diabetic mice (db/db) received the miS1 peptide in the form of eye drops (5 µL drops in each eye; 10 mg/mL; twice a day for 15 days; n=7 mice). Diabetic mice treated with the non-functional peptide Mut (n=7), treated with vehicle and non-diabetic mice (db/+) were used as controls. The eye drops were directly administered on the upper surface of the cornea of each eye using a micropipette. The weight and glycemia (colorimetric assay) were controlled throughout the study period. On day 15, the drop with the miS1 peptide or vehicle was administered about two hours before autopsy. The animals were euthanized by cervical dislocation and the enucleated eyes were immediately frozen and dorsoventral sections of 8 mm were cut for analyzing retinal morphology and other immunohistochemical analyses.

Glial activation was evaluated by means of GFAP (Glial fibrillar acidic protein) immunofluorescence following the methodology described in other studies (Bogdanov et al. PLoS One. 2014; 9:e97302). The fixed sections were blocked (1% BSA and 10% goat serum in PBS, 2 hours at RT) and incubated with anti-GFAP antibodies (dilution 1:500, 16 hours at 4° C.) followed by a secondary antibody (Alexa 488-conjugated goat anti-rabbit, dilution 1:200). The samples were contrasted with Hoesch and mounted for analysis under a confocal microscope. The images of diabetic and control samples were taken with identical parameters and the topographic distribution of the GFAP labelling was analyzed in a scale of 0 to 5 (Anderson et al. Clin Ophthalmol 2008; 2(4):801-16). A score of 1 indicates the absence of glial activation (positive immunofluorescence for GFAP restricted to the ganglion cell layer) whereas a score of 5 represents maximum glial activation (immunofluorescence for GFAP extends from the ganglion cell layer to the outer margin of the outer nuclear layer). Apoptosis was determined by means of TUNEL (Terminal Transferase dUTP Nick-EndLabeling; fluorescence kit) immunohistochemistry using the previously described method (Bogdanov et al. PLoS One. 2014; 9:e97302) and subsequent quantification under a fluorescence microscope. The retinal sections were permeabilized by means of incubation at room temperature for 5 minutes with a freshly prepared 20 µg/ml Proteinase K solution. The apoptotic cells were identified using green fluorescence [Alexa Fluor 594 goat-anti-rabbit (Invitrogen) (dilution 1:200 prepared in PBS)]. An excitation wavelength in the interval of 450-565 nm (e.g., 488 nm) was used for evaluation using fluorescence microscopy and the interval of 515-565 nm (green) was used for detection. The results are presented as the percentage of TUNEL positive cells with respect to Hoestchst staining cells obtained using Image J software.

The glutamate metabolism was evaluated in order to investigate the mechanisms through which the miS1 peptide produces neuroprotection. The glutamate concentration was determined by means of ultra-high performance liquid chromatography (UPLC) (Acquity-UPLC, Waters) MassTrak amino acid system). The GLAST (Glutamate/Aspartate transporter) was evaluated by means of immunofluorescence.

The paraffin sections were deparaffinized in xylene and rehydrated in a gradual series of ethanol. The sections were fixed in acidic methanol (−20° C.) for 1 minute and washed with 0.01 M phosphate buffered saline (PBS) at pH 7.4. After that, the antigens were recovered. The sections were submerged in an antigen recovery solution (10 mM sodium citrate, pH 6.0) and heated in a pressurized pot at 150° C. for 4 minutes. The sections were incubated in blocking solution (0.5% BSA and 10% goat serum in PBS) for 1 hour at room temperature. The sections were incubated with the rabbit anti-GLAST primary antibody (1:200, Abcam) overnight at 4° C. After one washing in PBS, the sections were incubated with an Alexa 488 goat anti-rabbit secondary antibody (1:200, Molecular Probes) for 1 hour at room temperature. The sections were washed in PBS, counter-stained with Hoechst (1:500, Sigma-Aldrich) and placed in a fluorescent mounting medium (Prolong, Invitrogen) with a cover glass. The GLAST immunofluorescence was quantified by means of laser confocal microscopy (Olympus FluoView™ FV1000 confocal microscope, Hamburg, Germany) using the ImageJ software.

The expression of IL-1β, TNF-α and IL-6 was evaluated. The total RNA was extracted with RNeasy Mini Kit with DNAse digestion (QIAGEN, distributed by IZASA, Barcelona, Spain) according to manufacturer's instructions. The RNA (1 µg) was used for reverse transcription with random hexanucleotide primers and Applied Biosystems reagents (Applied Biosystems, Madrid, Spain) in a reaction volume of 20 µl. The real time PCR was performed in a ABI Prism 7000 Sequence Detection System (Perkin-Elmer Applied Biosystems; Madrid, Spain) with SYBR Green Supermix; Applied Biosystems, Madrid, Spain). Each sample was assayed in triplicate and a negative control was included in each experiment. Human S18 was used as a control of endogenous gene expression. The ΔΔCt method was used for obtaining the relative quantification (RQ).

Electroretinogram (ERG) recordings were performed in darkness-adapted anesthetized mice (12 hours overnight). Focal electroretinogram (Ferg) recordings were measured using a Micron III Focal ERG system (Phoenix Research Labs, Pleasanton, Calif.). The recordings were taken with an electrode integrated in the corneal lens of the mouse mounted on the Focal ERG, a reference electrode placed in the head between the eyes, and an earth electrode placed in the tail. In addition, to assure than all the central retinas had been simulated, light stimuli were projected on the optical discs and the largest available light spot was used. (1.5 mm in diameter). The ERG responses of both eyes were recorded in response to 20 ms white light stimuli. The intensities of the white light stimuli were of 800, 3200 and 12800 cd·s·m−2 and an average of 6-10 consecutive flashes of light were made for each intensity. The ERG signals were amplified, the filtered band was between 0.5 and 1000 Hz, and was analyzed with LabScribe-2 software (BioSeb, Vitrolles, France) in order to calculate the a-wave and b-wave amplitude and implicit time, as recommended by the International Society of Clinical Electrophysiology of Vision (ISCEV) (Marmor et al Doc Ophtalmol 108: 107 a 144). The ERG recordings were performed at the start and on the day before euthanasia.

Treatment of the Disruption of the BRB Caused by Diabetes by Means of Ocular Topical Treatment With a SOCS1-Derived Peptide 8-week old diabetic mice (db/db) received the miS1 peptide in the form of eye drops (5 µL drops in each eye; 10 mg/mL; twice a day for 15 days; n=7 mice). Diabetic mice treated with vehicle (n=7) and non-diabetic mice (db/+) (n=7) were used as controls. The weight and glycemia (colorimetric assay) were controlled throughout the study period. The animals were euthanized on day 15 by cervical dislocation. The disruption of the BRB was evaluated by means of determining albumin permeability.

The paraffin sections were deparaffinized in xylene and rehydrated in a gradual series of ethanol. The sections were fixed in acidic methanol (−20° C.) for 1 minute and washed with 0.01 M PBS solution at pH 7.4. The sections were incubated in a blocking solution (2.5% dry, non-fat milk) for 30 minutes at room temperature. The sections were incubated with a goat anti-human serum albumin primary antibody (1:500, Abcam) overnight at 4° C. After one washing in PBS, the sections were incubated with an Alexa 594 donkey anti-goat secondary antibody (1:200, Molecular Probes) for 1 hour at room temperature. The sections were washed in PBS, counter-stained with Hoechst (1:500, Sigma-Aldrich) and placed in a fluorescent mounting medium (Prolong, Invitrogen) with a cover glass. The immunofluorescence of albumin was analyzed by means of laser confocal microscopy (Olympus FluoView™ FV1000 confocal microscope, Hamburg, Germany).

Treatment of Nephropathy and Atherosclerosis Caused by Diabetes by Means of Intraperitoneal Treatment With a SOCS1-Derived Peptide Apolipoprotein E (apoE)-deficient male mice of 8 weeks of age were made diabetic through streptozotocin injection (125 mg/kg weight in 10 mM citrate, pH 4.5, two consecutive days). After 2 weeks, animals with glycemia greater than 350 mg/dL were randomly distributed in two groups (n=9 animals per group): treated animals (miS1 peptide: 65 µg/day, 200 µL, intraperitoneally, every 2 days for 8 weeks) and controls (vehicle). The weight and glycemia (colorimetric assay) were controlled throughout the study period.

At the end of the study, the anesthetized animals were perfused with saline and sacrificed, processing the tissues immediately. In renal cortex (paraffin sections, 5 µm) the glomerular and tubulointerstitial morphology was studied by means of PAS and Masson trichrome staining and the lesions were evaluated in a double-blind and semi-quantitative manner in a scale of 0-3. Renal fibrosis was determined by means of Picro-Sirius red staining and the infiltrating inflammatory cells (F4/80+ macrophages and CD3+ T-lymphocytes) by immunohistochemistry. In the aorta, the root/arch zone (serial cryosections of 8 µm from the valves to an extension of 1000 µm) was stained with Oil-red-O/hematoxylin and the area of the atherosclerotic lesion was quantified (Metamorph program). Plaque stability was assessed by collagen fiber staining with Picro-Sirius red and α-actin immunofluorescence. The inflammatory component was determined by means of immunohistochemistry for monocyte/macrophages (Moma2). The Image Pro-Plus program was used for quantifying positive stainings. The biochemical parameters in serum (glycated hemoglobin, cholesterol and creatinine) and in urine (albumin and creatinine) were determined by means of conventional commercial kits.

In Vitro Studies

RAW264.7 macrophages and vascular smooth muscle cells (VSMC) cultured in a medium with 10% fetal bovine serum were used. The cells were synchronized (24 hours without serum), pre-incubated for 90 minutes with different peptide concentrations (miS1 or the control thereof, 50-150 µg/mL) and stimulated with cytokines (IFNγ 103 U/mL; IL-6 102 U/mL). STAT activation was analyzed by means of Western blot for phosphorylated STAT1/STAT3 isoforms. JAK/STAT pathway-dependent chemokine (CCL2) expression was determined by means of ELISA. Cell viability was analyzed by MTT colorimetric assay and macrophage migration was analyzed by chemotaxis assay.

Statistical Analysis

The results are expressed as mean±standard error of the total animals per group and of at least 3 independent cell cultures. The GraphPadPrism (ANOVA, Tukey and Student T-test; significance with P<0.05) program was used for statistical analysis.

Example 1: Effect of the Peptide of the Invention on Retinal Neurodegeneration

The miS1 peptide in the form of eye drops (50 µg in 5 µL/eye, twice a day) was locally administered in the model of type 2 diabetes (db/db mice) for 15 days. The progression of body weight and glucose levels is shown in FIG. 1.

Figure 3:
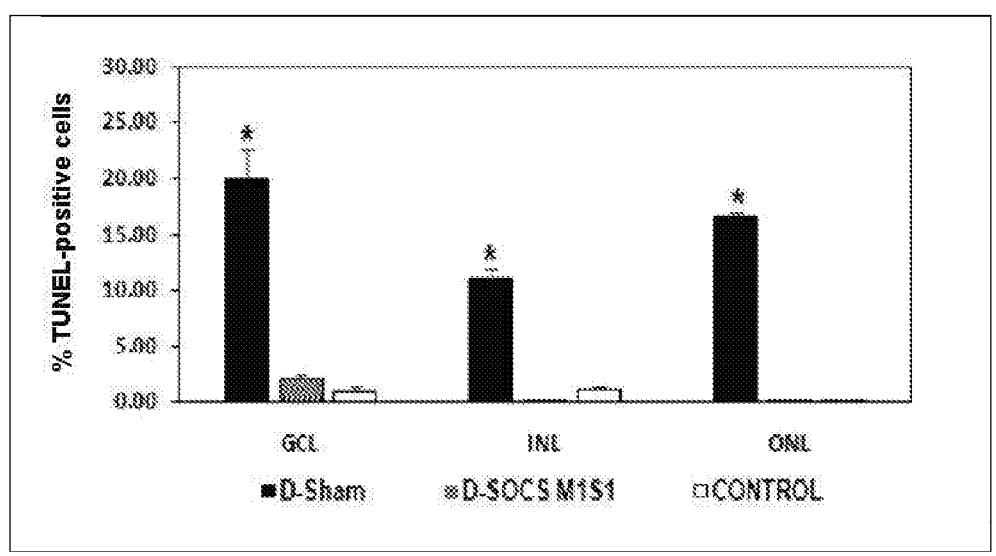
FIG. 3. Effect of the topical administration (eye drops) of the SOCS1-derived peptide on apoptosis. Percentage of positive cells measured by the TUNEL (Terminal Transferase dUTP Nick-EndLabeling) technique in the neuroretina of a representative mouse of each group, diabetic mice treated with vehicle [D-Sham], non-diabetic mice [control (db/+)] and diabetic mice treated with SOCS1-derived peptide [D-SOCSM1S1]. The results are expressed as mean±SD. *: $p<0.01$ compared with other groups.

Glial activation was measured with the GFAP marker (FIG. 2). As expected, GFAP expression in non-diabetic mice [control (db/+)] is limited mainly to the ganglion cell layer (GCL) of the retina (FIG. 2). Diabetic mice treated with vehicle [D-Sham] showed significantly greater GFAP expression than non-diabetic mice matched by age. Therefore, a 100% of the diabetic mice showed a GFAP score≥3. The two-week administration of the SOCS1-derived peptide resulted in a significant decrease of reactive gliosis, and the GFAP score of mice treated with SOCS1-derived peptide [D-SOCSMIS1] was 3 in all the cases (FIG. 2). The percentage of apoptotic cells in retinal layers (ONL, INL, and GCL) in diabetic mice [D-Sham] was significantly greater compared to that observed in the retinas of non-diabetic controls [control (db/+)] of the same age (FIG. 3). Diabetic mice treated with SOCS1-derived peptide [D-SOCSMIS1] showed a significantly lower apoptosis rate than diabetic mice treated with vehicle [D-Sham]. No differences were observed in the percentage of apoptotic cells between diabetic mice treated with the SOCS1-derived peptide [D-SOCSMIS1] and non-diabetic mice.

Figure 4A:
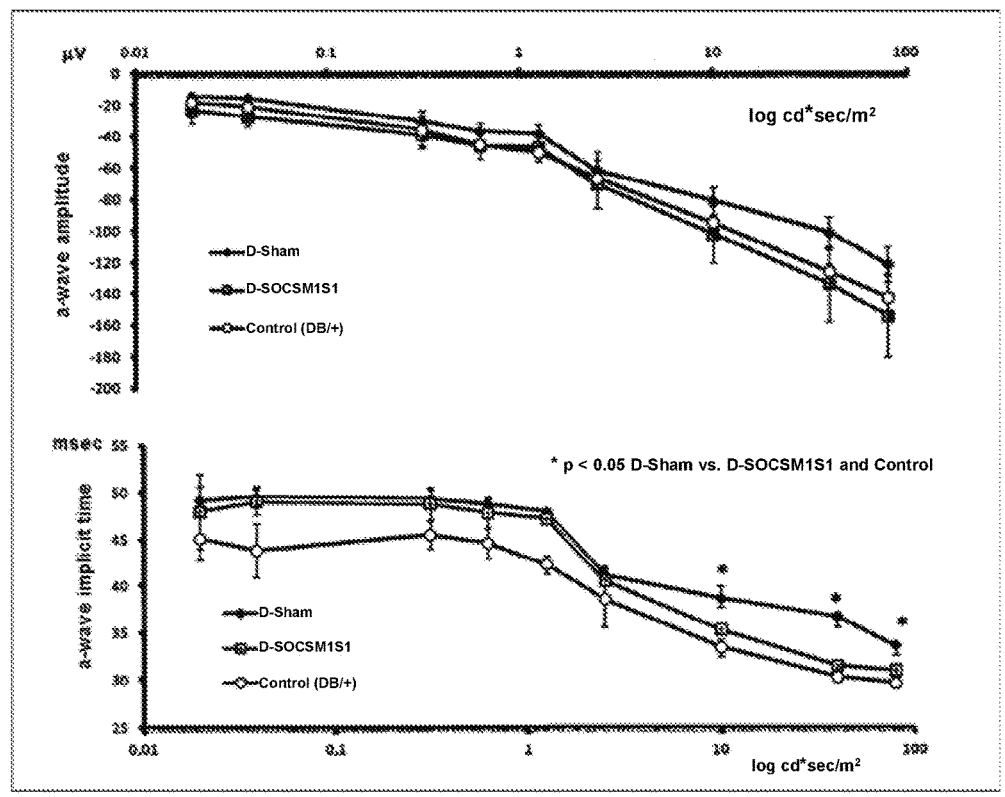
FIG. 4. Treatment with the SOCS1-derived peptide improves ERG abnormalities. (A) a-wave amplitude (top panel) and a-wave implicit time (bottom panel) in the experimental groups. (B) b-wave amplitude (top panel) and b-wave implicit time (bottom panel) in the experimental groups.
Figure 4B:
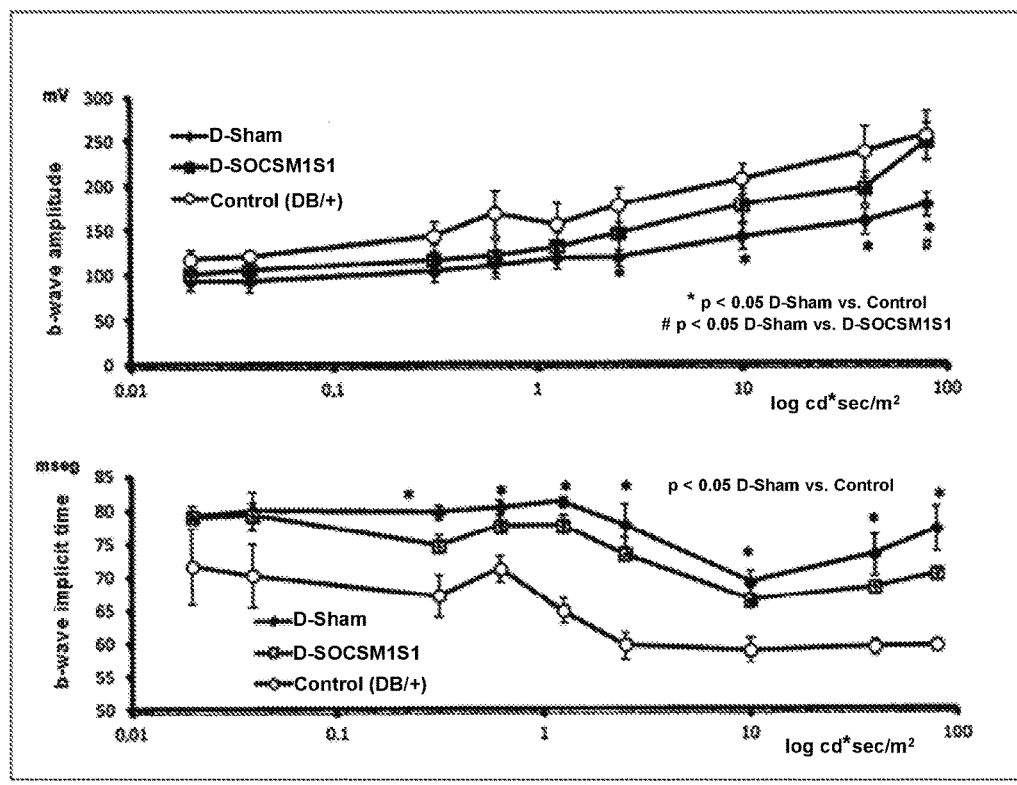

Treatment with the SOCS1-derived peptide declines the reduction of the a-wave and b-wave amplitude induced by diabetes, as well as the increase in the a-wave and b-wave implicit time (FIG. 4).

Figure 6A:
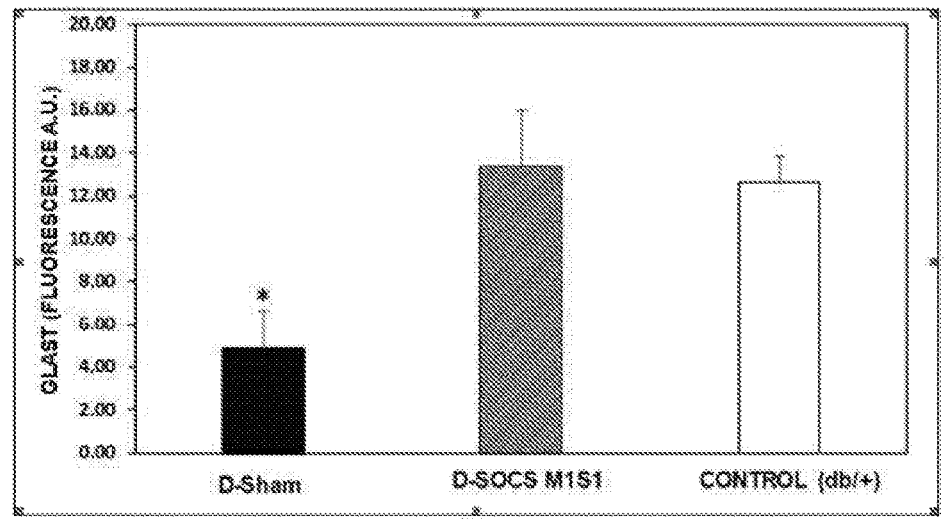
FIG. 6. Treatment with the SOCS1-derived peptide improves glutamate metabolism in diabetic mice. (A) GLAST immunofluorescence quantification in arbitrary units (A.U.). The results are expressed as mean±SD. (B) Retinal glutamate concentration measured by UPLC in the experimental groups. The results are expressed as mean±SD. *$p<0.001$ compared with other groups. **$p<0.01$ compared with the control group.
Figure 6B:
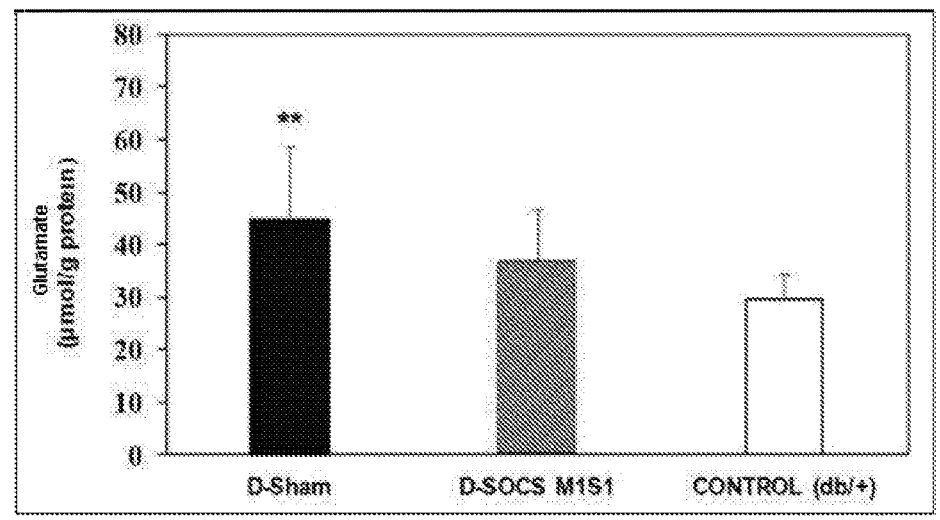

GLAST is the main glutamate transporter expressed by Müller cells since it is responsible for at least 50% of glutamate intake into the retina of mammals (FIG. 6A, top panel). The GLAST content was downregulated in the retinas of diabetic mice treated with vehicle [D-Sham]. In diabetic mice treated with the SOCS1-derived peptide [D-SOCSM1S1], GLAST downregulation was prevented (FIG. 6A, bottom panel). As a result, intraretinal glutamate levels were reduced but without reaching statistical significance (FIG. 6B). Therefore, among the mechanisms through which the miS1 peptide is a retinal neuroprotective agent, it must be pointed out that it prevents the increase in glutamate and the reduction in glutamate transporter, GLAST.

Figure 7:
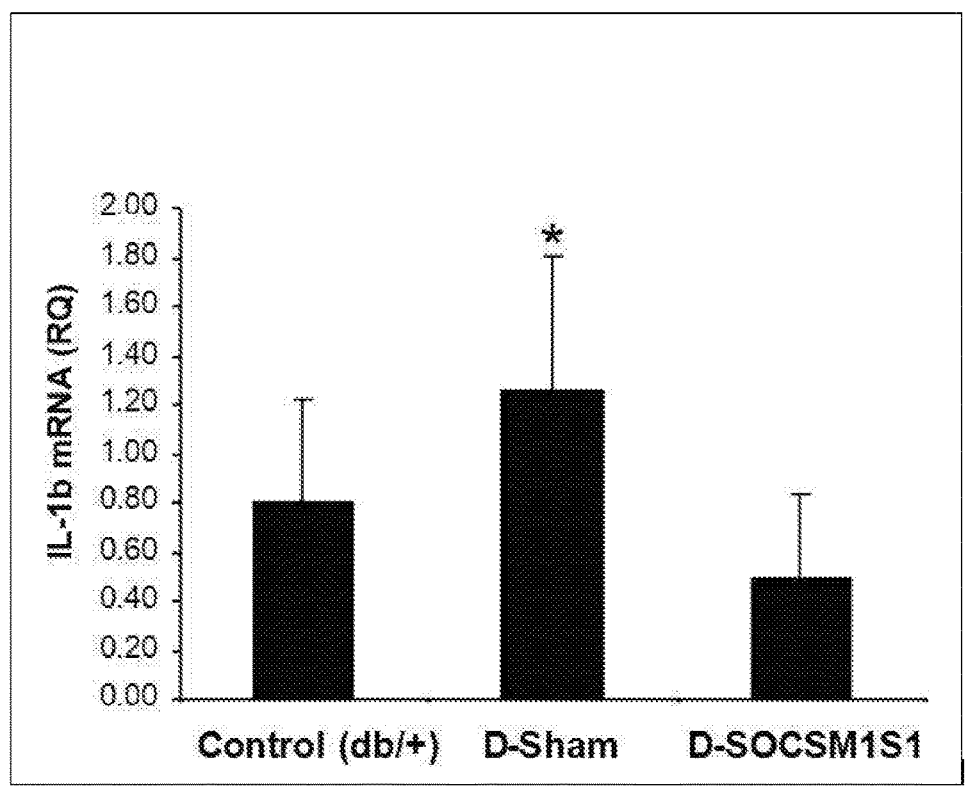
FIG. 7. SOCS1-derived peptide reduces inflammatory gene expression in diabetic retinopathy. IL-1β mRNA expression quantification using RT-PCR in diabetic mice treated with vehicle [D-Sham], non-diabetic mice [control (db/+)] and diabetic mice treated with SOCS1-derived peptide [D-SOCSM1S1]. The results are expressed as mean±SD. *$p<0.05$ compared with other groups. RQ: relative quantification.

Furthermore, the miS1 peptide prevented the increase in IL-1β induced by diabetes (FIG. 7). It must be pointed out that this cytokine plays a crucial role in the pathogenesis of diabetic retinopathy.

In conclusion, the administration of the miS1 peptide in the form of eye drops in diabetic mice prevented retinal neurodegeneration, determined by a significant reduction (about 80%) of GFAP glial protein staining and of apoptosis compared with groups that received Mut peptide or vehicle. The neuroprotective effect of the SOCS1-derived peptide was also proven by means of the functional examination of the retina (ERG).

These results demonstrate that the peptide of the invention is useful in the treatment of other diseases presenting with retinal neurodegeneration such as glaucoma and retinitis pigmentosa given that these diseases, like diabetes-induced retinal neurodegeneration, are characterized by the presence of glial inflammation and progressive neuronal death by apoptosis.

Example 2: Effect of the Peptide of the Invention on the Permability of the Blood-Retinal Barrier The miS1 peptide was locally administered in the model of type 2 diabetes (db/db mice) in the form of eye drops (50 µg in 5 µL/eye, twice a day) for 15 days. The progression of body weight and glucose levels is shown in FIG. 1.

Figure 5:
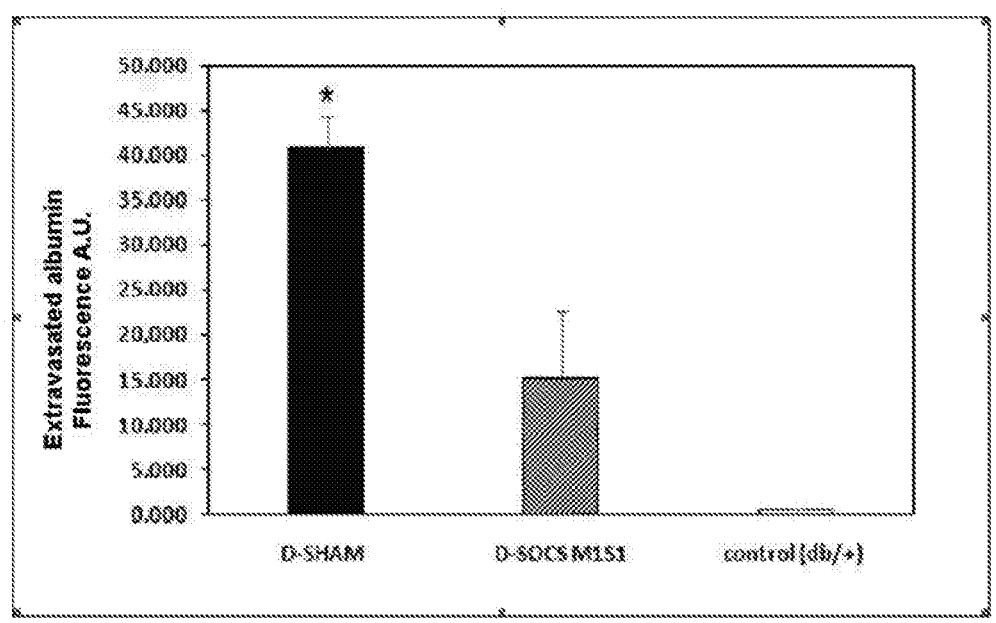
FIG. 5. Treatment with the SOCS1-derived peptide prevents diabetes-induced disruption of the BRB. Albumin extravasation quantification in arbitrary units of fluorescence (A.U.) evaluated in a representative diabetic mouse treated with vehicle [D-Sham], a diabetic mouse treated with the SOCS1-derived peptide [D-SOCSM1S1] and a non-diabetic mouse [control (db/+)]. The results are expressed as mean±SD *<0.01 compared with other groups.

Vascular permeability was evaluated by measuring albumin extravasation. Greater albumin extravasation was observed in db/db mice treated with vehicle [D-Sham] compared with control animals [control (db/+)]. Treatment with the SOCS1-derived peptide, miS1, prevented albumin extravasation in db/db mice [D-SOCSM1S1] (FIG. 5).

These results demonstrate that the peptide of the invention is useful in the treatment of diabetic macular edema given that said pathology occurs due to the disruption of the blood-retinal barrier, being characterized by the extravasation of fluid into the extravascular space (water and solutes; among the most abundant solutes is albumin) and the SOCS1-derived peptide according to the invention prevents said disruption.

Example 3: Effect of the Peptide of the Invention on Nephropathy and the Formation of Atheromatous Plaques in Diabetic Mice Systemic treatment with miS1 peptide (65 µg/day, every 2 days) was performed in the model of type 1 diabetes (streptozotocin in apoE mice) for 8 weeks. Table 1 shows the clinical and metabolic parameters at the end of the study. All the diabetic mice showed equivalent levels of hyperglycemia (glucose and glycated hemoglobin (HbA1c) and cholesterol, which indicates that the protective effect of the peptide is not due to a possible action on the glycemic control of these animals. Treatment with miS1 also significantly improved the renal function of diabetic mice, a decrease of 28% in albumin levels being observed. Furthermore, weight loss caused by chronic diabetes was less pronounced in the group treated with miS1 peptide.

Figure 8:
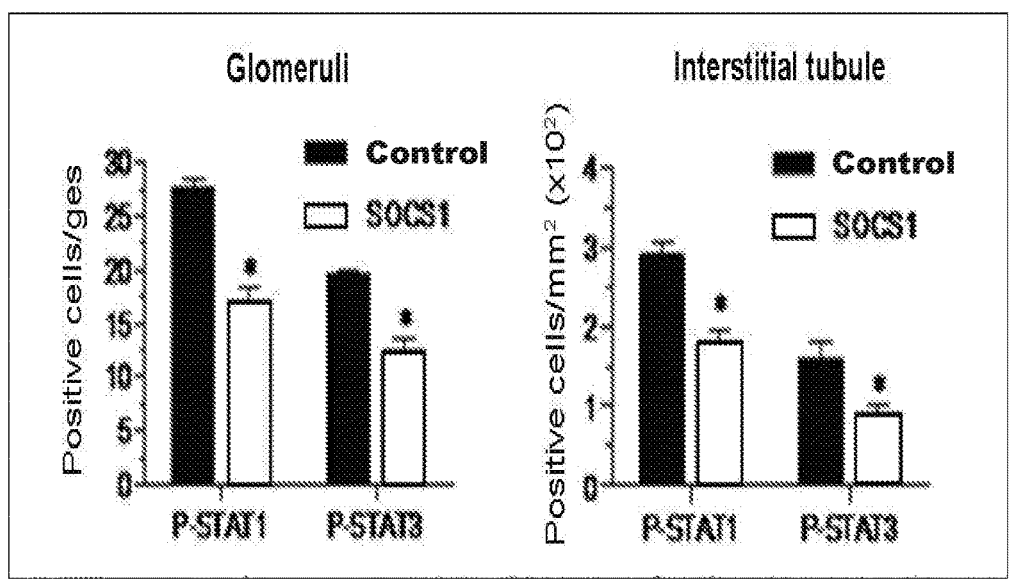
FIG. 8. SOCS1-derived peptide inhibits STAT activation in diabetic kidneys. The immunodetection of phosphorylated STAT1 and STAT3 was performed in kidney sections of diabetic mice. Quantification of positive staining in glomerular and tubulointerstitial compartments is shown. The results are expressed as mean±SD. *$p<0.02$ vs control group.
Figure 9A:
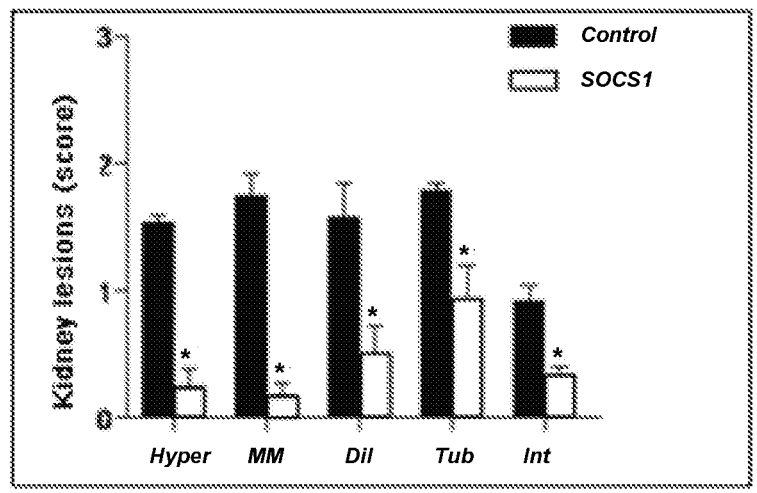
FIG. 9. Renoprotective effect of the SOCS1-derived peptide in diabetic mice. (A) Semi-quantitative evaluations of glomerular lesions (Hyper, hypercellularity, MM, mesangial matrix; Dil, capillary dilation), fibrosis and tubular degeneration (Tub) and fibrosis and interstitial inflammation (Int). (B) Morphometric analysis of the glomerular area. (C) Quantification of PAS+ mesangial area. The results are expressed as mean±SD. *$p<0.05$ vs control group.
Figure 9B:
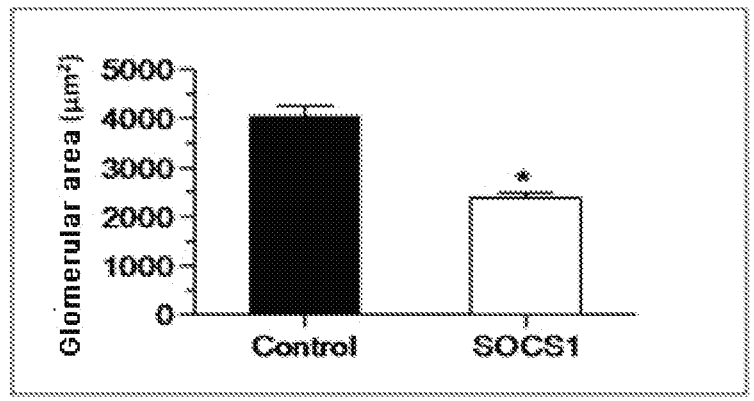
Figure 9C:
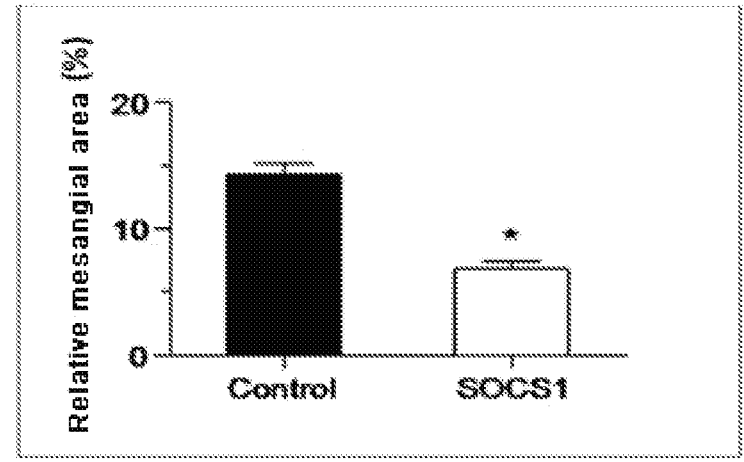
Figure 10A:
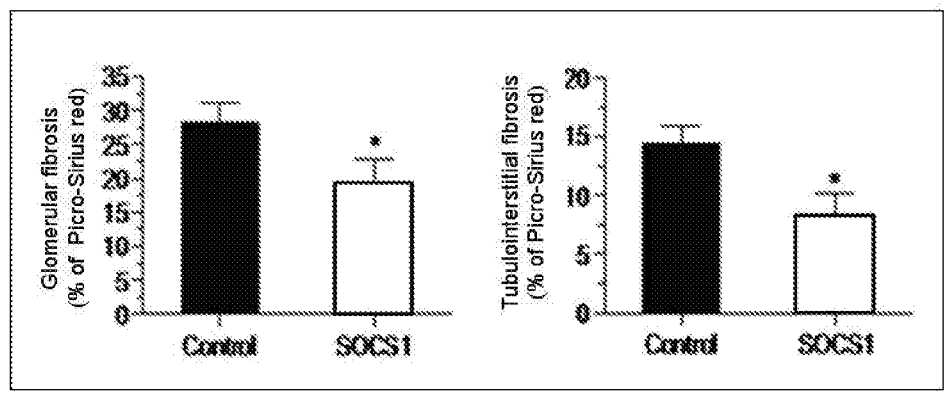
FIG. 10. SOCS1-derived peptide prevents renal fibrosis in diabetic nephropathy. (A) Quantitative analysis of collagen content in the glomerular and tubulointerstitial compartments in kidney samples from diabetic mice (control and SOCS1). (B) RT-PCR analysis of the mRNA expression of extracellular matrix proteins (fibronectin and type I collagen), the pro-fibrotic factor (TGF-β) and the tubular lesion marker (Kim-1) in the renal cortex. The data are expressed as mean±SEM. *$p<0.05$ vs control group.
Figure 10B:
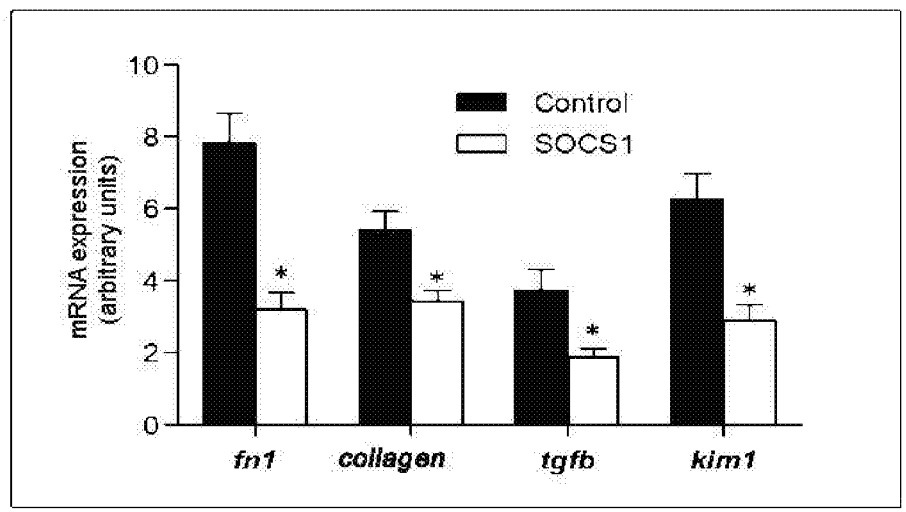
Figure 11A:
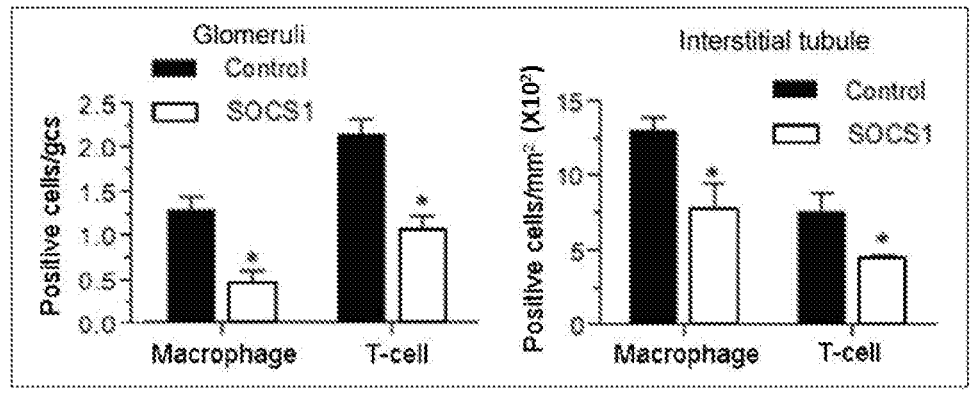
FIG. 11. Anti-inflammatory effect of the SOCS1-derived peptide on diabetic kidneys. (A) Immunoperoxidase detection of macrophage (F4/80) and T-lymphocyte (CD3) infiltration in kidney samples from diabetic mice. The quantification of positive cells in glomeruli and interstitial tubule is shown. (B) RT-PCR analysis of the mRNA expression of chemokines (CCL2 and CCL5) and TNFα cytokine in the renal cortex. The data are expressed as mean±SEM. *$p<0.05$ vs control group.
Figure 11B:
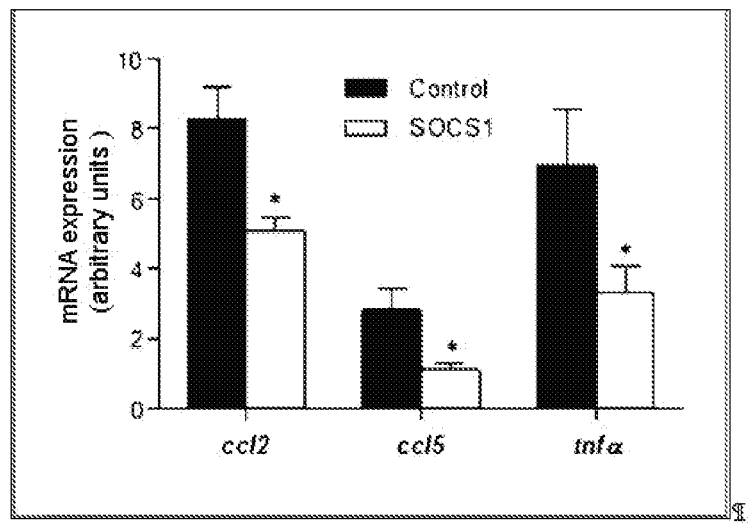
Figure 12A:
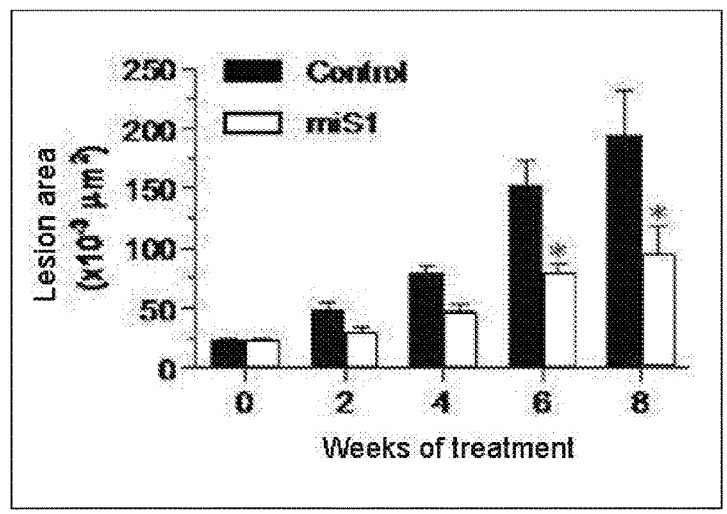
FIG. 12. Anti-atherosclerotic effect of the miS1 peptide on experimental diabetes. (A) Progression of atheromatous plaque size over time in transverse aorta sections of diabetic mice. (B) Quantification of the inflammatory content (Moma2 macrophage staining) and plaque stability markers (staining of collagen fibers with Sirius red and vascular cells with α-actin) in atherosclerotic lesions of diabetic mice. *, $p<0.05$ vs control group.
Figure 12B:
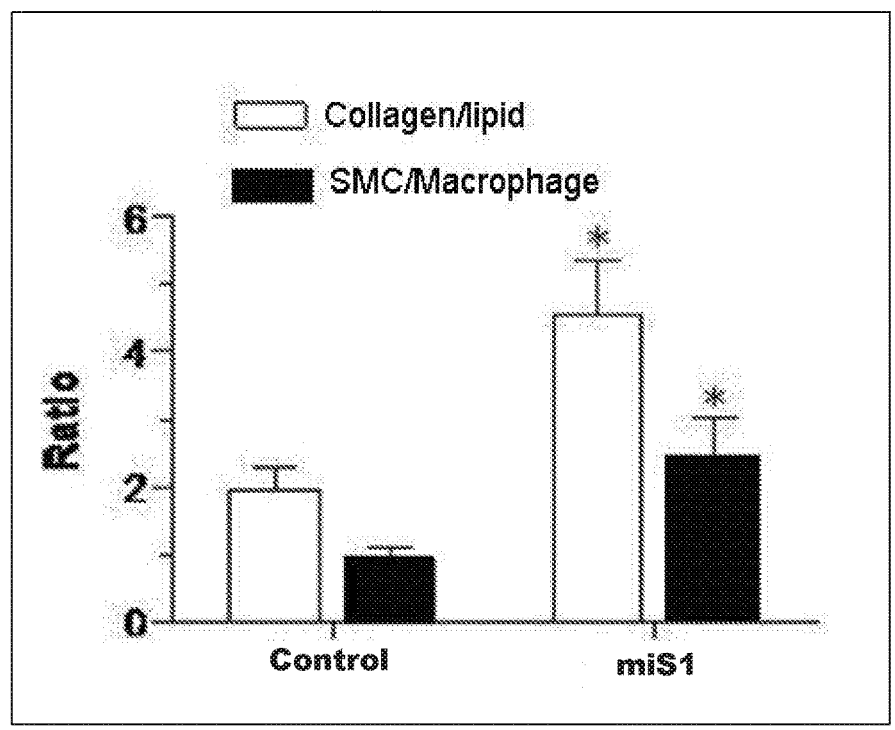

The histological analysis in kidney sections of diabetic mice demonstrated a reduction in renal STAT1 and STAT3 activation (FIG. 8) together with an improvement of glomerular lesions (hypercellularity, mesangial expansion and glomerular hypertrophy) and tubulointerstitial lesions (atrophy, degeneration and infiltrate) in the group treated with miS1 peptide compared with diabetics that received the vehicle (FIG. 9). The miS1 peptide significantly reduced tubulointerstitial fibrosis (FIG. 10) and inflammatory lymphocyte and macrophage infiltrate (FIG. 11). The anti-atherosclerotic properties of treatment with miS1 peptide in diabetic mice are studied in another series of experiments. Atheromatous plaques staining with Oil-red-O/hematoxylin and the subsequent quantification thereof showed a significant reduction in the size and extension of the lesions in diabetic mice treated with miS1 peptide (50% reduction compared with the control group that received the vehicle; FIG. 12A). The analysis of the plaque composition showed a reduction in the number of macrophages in the lesions of the treated animals, as well as a higher collagen and vascular cells content (FIG. 12B), therefore indicating that the treatment reduced inflammation and improved the stability of atheromatous plaques in the diabetic animals.

TABLE 1

Metabolic and renal data in mice with type 1 diabetes

| Parameter | Control | SOCS1 |
|---|---|---|
| Weight (g) | 21.3 ± 0.9 | 21.9 ± 0.6 |
| Blood glucose (mg/dL) | 528 ± 12 | 549 ± 29 |
| GHbA1c (ug/mL) | 470 ± 74 | 503 ± 76 |
| Total cholesterol (mg/dL) | 583 ± 19 | 611 ± 59 |
| LDL cholesterol (mg/dL) | 557 ± 19 | 597 ± 61 |
| HDL cholesterol (mg/dL) | 12 ± 1 | 11 ± 1 |
| Triglycerides (mg/dL) | 72 ± 5 | 89 ± 23 |
| AST (U/L) | 226 ± 16 | 176 ± 20 |
| ALT (U/L) | 106 ± 6 | 97 ± 17 |
| Kidney-body mass ratio (mg/g) | 20.5 ± 1.1 | 16.4 ± 1.3 ($p < 0.05$) |
| Serum creatinine (mg/dL) | 0.40 ± 0.04 | 0.24 ± 0.04 ($p < 0.02$) |
| Urine albumin-creatinine ratio (ug/umol) | 22.6 ± 1.4 | 16.2 ± 61.1 ($p < 0.01$) |

Example 4: In Vitro Studies

Figure 13A:
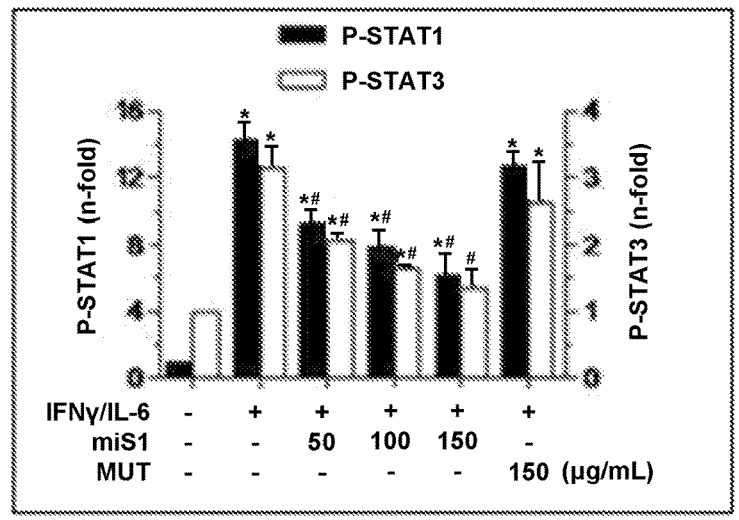
FIG. 13. In vitro effects of the SOCS1-derived peptide and the inactive mutant control thereof. (A) STAT1 and STAT3 activation in macrophages stimulated with cytokines in the presence of different concentrations of the SOCS1-derived peptide or mutant peptide. (B) Production of the CCL2 chemotactic protein in macrophages and VSMC. (C) Macrophage migration assay. *, $p<0.05$ vs baseline conditions; #, $p<0.05$ vs stimulation with cytokines.
Figure 13B:
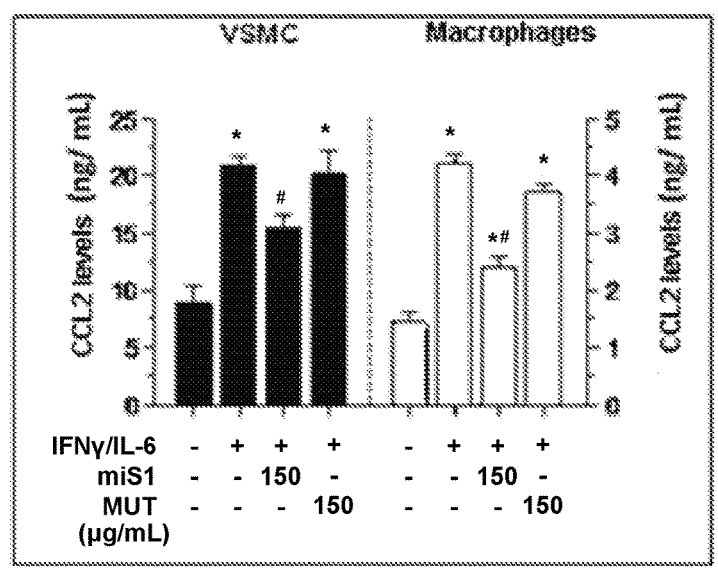
Figure 13C:
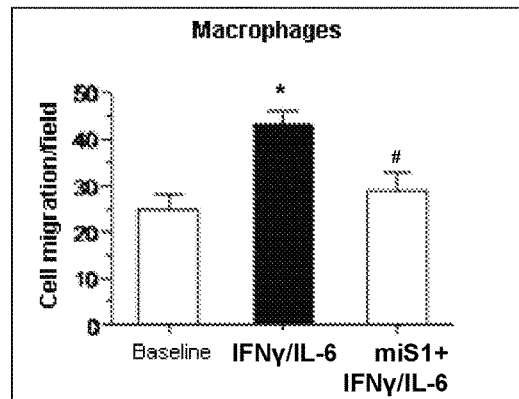

Murine macrophages and primary cultures of mouse vascular smooth muscle cells (FIG. 13) were used in the in vitro studies. In both cases, activation of the JAK/STAT pathway was induced by stimulation with proinflammatory cytokines IFNγ and IL-6. The pre-incubation of macrophages with increasing concentrations (50-150 ug/mL) of the inhibitory peptide miS1 reduced STAT1 and STAT3 activation in a dose-dependent manner (determined by the phosphorylation levels of both proteins in a Western blot assay). In contrast, a similar dose of the Mut peptide (150 ug/mL) did not cause any effect, the specificity of the inhibitory peptide miS1 thus being confirmed. Similarly, the miS1 peptide prevented STAT1 and STAT3 activation in VSMC, as can be seen in the immunofluorescence images. To determine the functional consequences of the inhibition by the miS1 peptide, the secretion of monocyte chemotactic protein CCL2, the expression of which depends on the JAK/STAT pathway, was analyzed. The pre-incubation with the inhibitory peptide miS1, but not with the Mut peptide, significantly reduced (30-40%) cytokine-induced CCL2 production both in VSMC and in macrophages. Finally, the anti-migratory effect of the inhibitory peptide miS1 in macrophages was confirmed by means of chemotaxis assays. No variations in the cell viability of VSMC and macrophages were observed in any of the studied experimental conditions, which indicates the non-toxicity of the peptide at the concentrations used.

Example 5: Justification That the Provided Data Can Be Extrapolated to Humans The animal and cell models used in the examples of the present invention are accepted in the medical and pharmaceutical sector as models that allow extrapolating the data obtained by means of use thereof to human diseases. On one hand, the apolipoprotein E gene-deficient mouse is characterized by having a deficient reverse cholesterol transport determining a systemic hypercholesterolemia with high lipid and cholesterol accumulation in adipose and peripheral tissues. This mouse model spontaneously develops (in an accelerated manner if it is fed with a fatty diet) atheromatous lesions with some characteristics similar to human lesions. To that end, it is one of the most widely used models in cardiovascular research. Secondly, the induction of type 1 diabetes in apoE mice is an experimental model that combines hyperglycemia and hyperlipidemia (two risk factors in these pathologies) and are characterized by a rapid development of atherosclerosis and nephropathy as a result of diabetes. Finally, the db/db mouse is characterized by leptin receptor deficiency, spontaneous development of type 2 diabetes and obesity at 4-8 weeks of age and a subsequent retinal neurodegeneration process very similar to that occurring in the initial stages of diabetic retinopathy in diabetic patients.

The invention claimed is:

1. A method of treatment of a disease of diabetic retinopathy, or diabetic nephropathy, which method comprises administering to a patient in need of such treatment a therapeutically effective amount of an isolated polypeptide comprising
   a) the sequence of DTHFRTFRSHADYRRI (SEQ ID NO: 2); or
   b) a variant of the sequence of a) which is at least 85% identical to SEQ ID NO: 2, based on the identity of all the amino acids of said sequence,
   wherein at least one amino acid of the sequence of the isolated polypeptide is phosphorylated.

2. The method according to claim 1, wherein the disease is diabetic retinopathy.

3. The method according to claim 1, wherein the sequence SEQ ID No: 2 or the at least 85% identical variant of the isolated polypeptide is bound to a cell permeability region.

4. The method according to claim 1, wherein the sequence SEQ ID NO: 2 or the at least 85% identical variant of the isolated polypeptide is bound to a cell permeability region, wherein the cell permeability region is lysine-palmitate.

5. The method according to claim 1, wherein the sequence SEQ ID NO: 2 or the at least 85% identical variant of the isolated polypeptide is bound to a cell permeability region, wherein the cell permeability region is bound at the N-terminal end of the peptide sequence.

6. The method according to claim 1, wherein the isolated polypeptide consists essentially of
   a) the sequence of SEQ ID NO: 2; or
   b) a variant of the sequence of a) which is at least 85% identical to SEQ ID NO:
   2, based on the identity of all the amino acids of said sequence.

7. The method according to claim 1, wherein the isolated polypeptide consists essentially of
   a) the murine SOCS 1 protein (UniProt: O35716);
   b) the human SOCS 1 protein (UniProt: O15524); or
   c) a variant of the sequence of a) or b) which is at least 85% homologous to the amino acid sequence of the murine SOCS 1 protein or to the amino acid sequence of the human SOCS 1 protein.

8. The method according to claim 1, wherein the isolated polypeptide consists in the sequence SEQ ID NO: 2 bound to a cell permeability region.

9. The method according to claim 1, wherein at least one of the phosphorylated amino acids is a tyrosine (Y) amino acid.

10. The method according to claim 1, wherein the therapeutically effective amount of the isolated polypeptide is administered with at least one pharmaceutically acceptable vehicle or excipient.

11. The method according to claim 1, wherein the therapeutically effective amount of the isolated polypeptide is administered with at least one pharmaceutically acceptable vehicle or excipient, wherein the administration is performed orally, gastroenterically, parenterally, rectally, by respiratory route or topically, or ophthalmically.

12. The method according to claim 1, wherein the therapeutically effective amount of the isolated polypeptide is administered with at least one pharmaceutically acceptable vehicle or excipient, wherein the disease is diabetic retinopathy.

13. The method according to claim 1, wherein the therapeutically effective amount of the isolated polypeptide is administered with at least one pharmaceutically acceptable ophthalmic vehicle or excipient, wherein the disease is diabetic retinopathy.

14. The method according to claim 1, wherein the therapeutically effective amount of the isolated polypeptide is administered with at least one pharmaceutically acceptable vehicle or excipient, wherein the administration is performed ophthalmically.

15. The method according to claim 5, wherein the N-terminal end of the peptide sequence is aspartic acid.

* * * * *

SEQUENCE LISTING

<160> NUMBER OF SEQ ID NOS: 8

<210> SEQ ID NO 1
<211> LENGTH: 16
<212> TYPE: PRT
<213> ORGANISM: Artificial Sequence
<220> FEATURE:
<223> OTHER INFORMATION: A synthetic "kinase inhibitory region" of
      murine SOCS1 protien

<400> SEQUENCE: 1

Asp Thr His Phe Arg Thr Phe Arg Ser His Ser Asp Tyr Arg Arg Ile
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: A synthetic "kinase inhibitory region" of human
      SOCS1 protien

<400> SEQUENCE: 2

Asp Thr His Phe Arg Thr Phe Arg Ser His Ala Asp Tyr Arg Arg Ile
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: A synthetic mutated peptide (Mut)

<400> SEQUENCE: 3

Asp Thr His Ala Arg Thr Ala Arg Ser His Ser Asp Tyr Arg Arg Ile
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: A synthetic permeability sequence

<400> SEQUENCE: 4

Tyr Gly Arg Lys Lys Arg Arg Gln Arg Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: A synthetic permeability sequence

<400> SEQUENCE: 5

Arg Gln Ile Lys Ile Trp Phe Gln Asn Arg Arg Met Lys Trp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: A synthetic permeability sequence

<400> SEQUENCE: 6

```
Arg Arg Gln Arg Arg Thr Ser Lys Leu Met Lys Arg
1               5                   10

<210> SEQ ID NO 7
<211> LENGTH: 8
<212> TYPE: PRT
<213> ORGANISM: Artificial Sequence
<220> FEATURE:
<223> OTHER INFORMATION: A synthetic permeability sequence

<400> SEQUENCE: 7

Lys Lys Lys Lys Lys Lys Lys Lys
1               5

<210> SEQ ID NO 8
<211> LENGTH: 6
<212> TYPE: PRT
<213> ORGANISM: Artificial Sequence
<220> FEATURE:
<223> OTHER INFORMATION: A synthetic permeability sequence

<400> SEQUENCE: 8

Arg Arg Arg Arg Arg Arg
1               5
```